United States Patent
Hörnemann

[19]

[11] Patent Number: 5,807,749
[45] Date of Patent: Sep. 15, 1998

[54] METHOD FOR DETERMINING THE CALORIFIC VALUE OF A GAS AND/OR THE WOBBE INDEX OF A NATURAL GAS

[75] Inventor: Johan Adrianus Tilmann Hörnemann, Apeldoorn, Netherlands

[73] Assignee: Gastec N.V., Apeldoorn, Netherlands

[21] Appl. No.: 815,325

[22] Filed: Mar. 10, 1997

Related U.S. Application Data

[63] Continuation of Ser. No. 424,290, filed as PCT/NL93/00213, Oct. 25, 1993, published as WO94/10566, May 11, 1994, abandoned.

[30] Foreign Application Priority Data

Oct. 23, 1992 [NL] Netherlands ............................ 9201845

[51] Int. Cl.⁶ .................................................. G01N 25/22
[52] U.S. Cl. ................................ 436/143; 374/36; 374/37
[58] Field of Search .............................. 436/143; 374/36, 374/37

[56] References Cited

U.S. PATENT DOCUMENTS

| | | |
|---|---|---|
| 3,460,909 | 8/1969 | Gayle . |
| 3,678,489 | 7/1972 | Scherban et al. .......................... 340/511 |
| 4,020,480 | 4/1977 | Gotley et al. ............................. 340/237 |
| 4,386,858 | 6/1983 | Kude et al. ................................. 374/37 |
| 4,396,299 | 8/1983 | Clingman, Jr. et al. ................... 374/37 |
| 4,677,841 | 7/1987 | Kennedy ..................................... 73/30 |
| 4,783,168 | 11/1988 | Florisson et al. ......................... 356/301 |
| 4,951,503 | 8/1990 | Fini ............................................ 374/36 |
| 5,012,432 | 4/1991 | Stetter et al. ............................... 374/37 |
| 5,167,450 | 12/1992 | Nukui et al. ................................ 374/36 |
| 5,288,149 | 2/1994 | Meyer ......................................... 374/37 |

FOREIGN PATENT DOCUMENTS

| | | |
|---|---|---|
| 0213073 | 8/1987 | European Pat. Off. . |
| 0304266 | 2/1989 | European Pat. Off. . |
| 0445861 | 9/1991 | European Pat. Off. . |
| 1471088 | 2/1967 | France . |
| 506213 | 8/1930 | Germany . |

OTHER PUBLICATIONS

Hawley's Condensed Chemical Dictionary, Van Nostrand Reinhold, twelfth edition, pp. 175, 982, 996, 1111, 1112, 1993.

Chromatography, fundamentals and aplications of chromathographic and electrophoretic methods, part A: fundamentals and techniques, edited by Heftmann, Elsevier Scientific Publishing Company, p. A11, 1983.

*Primary Examiner*—Jill Warden
*Assistant Examiner*—Alexander Markoff
*Attorney, Agent, or Firm*—Weingarten, Schurgin, Gagnebin & Hayes LLP

[57] ABSTRACT

A method and apparatus for determining the calorific value of a combustible gas including passing an amount of gas through a hydrocarbon detection device comprising interconnected first and second measuring cells, the first measuring cell including a catalyzing substance, wherein the first and second measuring cells provide a signal, the signal is integrated to determine a value, and the value is compared with calibrated values to determine the calorific value. In another embodiment, the Wobbe index of natural gas is determined further including determining the density of the gas and calculating the Wobbe index from the calorific value and density.

13 Claims, 3 Drawing Sheets

METHOD FOR DETERMINING THE CALORIFIC VALUE OF A GAS AND/OR THE WOBBE INDEX OF A NATURAL GAS

This application is a continuation of Ser. No. 424,290, filed as PCT/NL93/00213, Oct. 25, 1993, published as WO94/10566, May 11, 1994, now abandoned.

BACKGROUND OF THE INVENTION

1. Field of the Invention

The present invention relates to a method for determining the calorific value of a combustible gas. The invention further relates to a method for determining the Wobbe index of natural gas.

2. Description of the Prior Art

The determination of the calorific value of combustible gasses, such as natural gas and other fuel gasses, can be of importance for various reasons.

It is a fact that when natural gas from different sources is used, the composition, and therefore the calorific value, of the various gasses is not the same. For a buyer it may be of importance to know the calorific value so as to compensate fluctuations in conditions of use. Also, it is common for the price of the gas to be related to its calorific value.

The calorific value of a gas can be determined by burning the gas under conditions whereby the heat of combustion is measured. From the various data of the gas sample, such as mass, heat content, rise in temperature and the like, the calorific value can be accurately calculated. Such a method, however, is cumbersome and time-consuming, and therefore not suitable for the rapid in situ determination of the calorific value of the gas.

Accordingly, there is a need for a method which enables the calorific value of a combustible gas to be determined rapidly and accurately.

As regards the Wobbe index, too, it is important that it can be determined rapidly and accurately.

SUMMARY OF THE INVENTION

The invention accordingly relates to a method for determining the calorific value of a combustible gas, which method is characterized in that an accurately determined amount of gas is passed through a detection device, the signal obtained is integrated, the value thus obtained is compared with a calibration line and the calorific value is calculated therefrom.

The invention further relates to a method for determining the Wobbe index of natural gas, which method is characterized in that an accurately determined amount of natural gas is passed through a detection device, the signal obtained is integrated, the value thus obtained is compared with a calibration line and the Wobbe index is calculated from the calorific value thus obtained, combined with the density of the gas.

As a detection device, use is preferably made of a hydrocarbon detector based on catalytic combustion, more particularly a methane detector. Such detectors are commercially available and comprise inter alia a combustion chamber in which a temperature-sensitive resistance wire is located having applied thereto a catalyst for the catalytic combustion of hydrocarbons. If this wire comes into contact with a combustible gas, a combustion occurs whereby the resistance of the wire changes. This change can be ascertained, for instance with a Wheatstone bridge.

Surprisingly, it has now been found that it is possible to pass a known amount of gas through such a detection device and to obtain a reliable value for the calorific value from the measuring result. This is particularly unexpected since such detectors are not based on combustion of the total amount of gas but only on a part thereof. It has nonetheless been found that the signal of such a detector can be used for obtaining a reliable measuring result.

Accordingly, if an exactly known amount of combustible gas, such as natural gas, is passed through a hydrocarbon detector, the result obtained after integration of the signal, i.e., after determination of the area under the curve, is a value which upon comparison with a calibration line accurately indicates the calorific value of the gas.

In the case where the Wobbe index of natural gas is to be determined, the determination of the calorific value as described above can be combined with a determination of the density of the natural gas, for instance with a katharometer. When using a katharometer for determining the density of the gas, the heat conductivity of the gas is determined with this meter. This quantity can subsequently be converted to the density of the gas, for instance with the aid of a calibration line. The determination can be performed on the same sample stream as that of which the calorific value is determined. This can for instance occur in parallel, or prior to the determination of the calorific value. The Wobbe index is obtained from the thus obtained data for the calorific value and the density.

An important advantage of the method according to the invention is the simplicity, speed and accuracy with which the determinations can be carried out. It is possible to carry out a determination within a few tens of seconds. This can be of great importance, in particular for process control or large scale consumption of gas. The accuracy of the determination of the calorific value appears to be very good; the error is less than 0.05 %.

According to the invention, it is for instance possible to allow the gas whose calorific value is to be determined to flow from a mainstream through a sampling conduit, whereafter the sampling conduit is shut off from the mainstream and is brought into communication with a sampling stream and the contents of the sampling conduit is passed entirely through the detection device. If desired, the gas can be diluted. The method according to the invention can simply be carried out with the aid of a plurality of cocks, for instance two four-way cocks which are connected as described in the drawing. Naturally, it is also possible to utilize other designs, for instance starting from two, three or six-way cocks. Such a system can be advantageously controlled with the aid of a computer which provides not only for the control of the apparatus but also for the calculation of the calorific value and/or the Wobbe index.

Other methods where an exact amount of gas is supplied to a measuring device are also applicable. For instance, use could be made of a system based on pulse techniques. Thus, it is also possible to supply the gas to the detector pulsewise. In that case, a sine-shaped measured signal can be obtained, whose amplitude is a measure of a calorific value.

The present invention can be used for determining the calorific value of various types of combustible gas. Examples include natural gas, synthesis gas, fuel gas, refinery gas and pyrolysis gas.

The invention also relates to an apparatus for determining the calorific value of a combustible gas, comprising a hydrocarbon detector, means for supplying an accurately determined amount of gas to the detector, means for determining the signal of the detector, means for integrating the signal thus determined and means for comparing the integrated signal with calibration values and calculating the calorific value of the gas.

An apparatus for determining the Wobbe index of natural gas comprises the same components as the apparatus for determining the calorific value of a gas, with means added thereto for determining the density of the natural gas and means for calculating the Wobbe index from the density and the calorific value.

The invention will now be elucidated with reference to some drawings.

DESCRIPTION OF THE PREFERRED EMBODIMENTS

Figure 1:
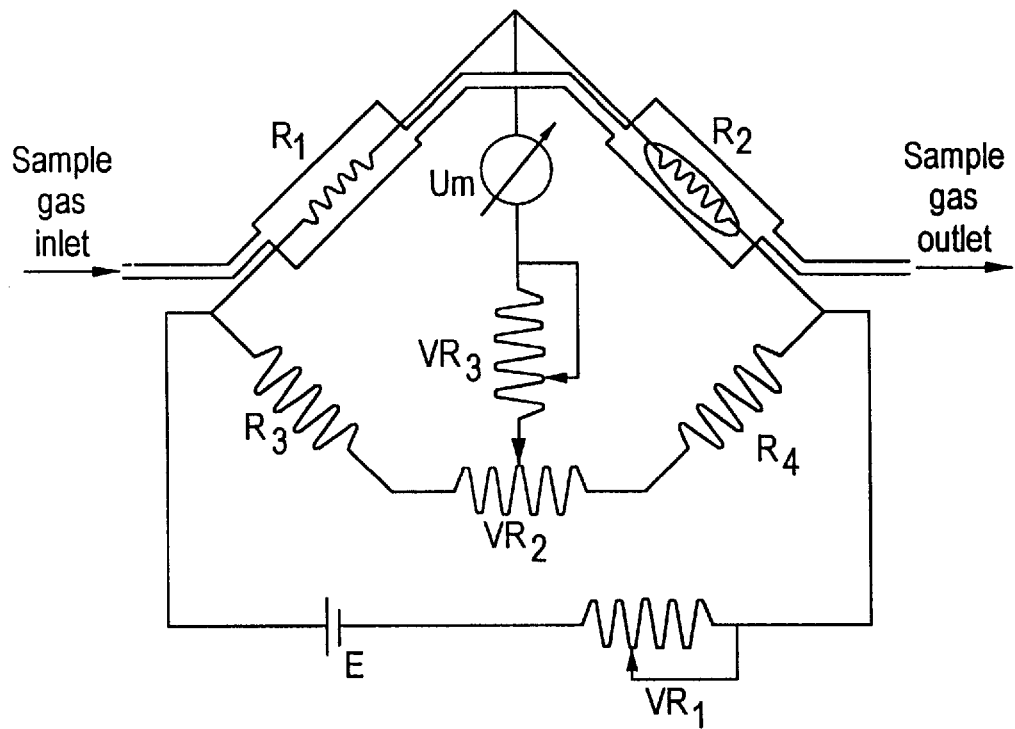
FIG. 1 is a schematic representation of one embodiment of a detector device in accordance with the present invention.

In FIG. 1 the principle of the measurement is elucidated.

The sample gas flows through two measuring cells in which filaments $R_1$ en $R_2$ are arranged. Filament $R_2$ is provided with a catalyzing substance. If a combustible gas is present in the sample air passing through, the heat production of $R_2$, as a result of the catalytic combustion, will be greater than at $R_1$. As a result of the additionally produced heat, the temperature of $R_2$ and therefore the electric resistance of $R_2$ becomes higher than that of $R_1$.

The electric equilibrium of the bridge circuit is removed and the resultant measured signal $U_m$ is a measure for the additionally produced heat of $R_2$.

The temperature of the filaments and the catalyst is set with $Vr_1$. With $Vr_2$ the zero point is set. With $Vr_3$ the span is set.

The reference cell and the catalytic measuring cell are thermally coupled. Both cells are accommodated in a solid thermally inert measuring block. As a result, variations in ambient temperature and the temperature of the sample air have only a minimum influence on the measured signal.

Figure 2:
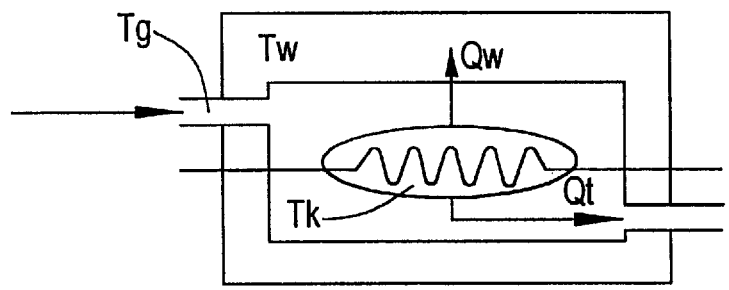
FIG. 2 is a schematic representation of an exemplary measuring cell for the detector device of FIG. 1.

FIG. 2 schematically shows a possible measuring cell. In stationary condition, with a fixed air/gas ratio, the produced heat of the filament will be removed partly to the cell wall and partly by the air stream.

$$Qf = C_1(T_k - T_g) \qquad Q_w = C_2(T_k - T_w)$$
$$Q1 = Qj + Q_w = C_1(T_k - T_g) + C_2(T_k - T_w)$$
$$= C_1T_k - C_1T_g + C_2T_k - C_2T_w$$
$$U_m = C_m \times Q1 = (C_1 + C_2)T_k - C_1T_g - C_2T_w$$
$$U_m = C_m\{(C_1 + C_2)T_k - C_1T_g - C_2T_w\}$$

In case of a small modification of the air/gas ratio or the gas composition, first a modification of Tk will arise.

$$U_m = C_m\{(C_1+C_2)\Delta T_n - C_1T_g - C_rT_w\}$$

Owing to the thermal inertia of the measuring block, $T_w$ will adjust after some time to a new thermal equilibrium. The consequence is that $U_m$ will achieve an equilibrium value only after some time has passed.

The temperature of the air supplied also affects $U_m$. If a small amount of the gas to be measured is introduced into the air stream of the measuring cell, $T_w$ will hardly change during the passage of the gas owing to the thermal inertia. The measured signal is not subject to the influence of this inertia.

Figure 3:
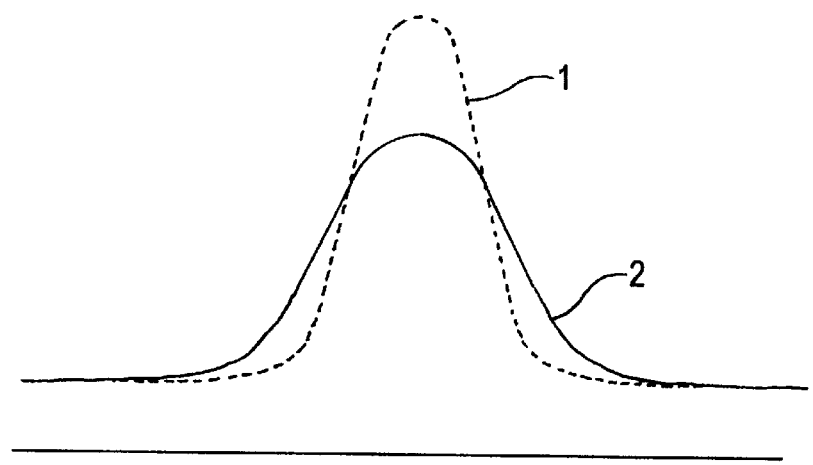
FIG. 3 is a graphical depiction of energy generated by catalytic combustion associated with the detector device of FIG 1.

When a sample loop is used, the measured signal has the shape of a Gaussian curve. The area of the curve is proportional to the energy generated by the catalytic combustion. Modification of the air stream results in the curve becoming more or less sharp (curves 1 and 2 of FIG. 3). The area of the Gaussian curve, however, remains constant.

The integrated value of the measured signal always gives a good value for the generated energy of the combusted amount of gas. When a single measuring cell is used, the maximum of the curve will be affected by $T_g$ and $T_w$. By using a non-catalytically active reference cell, connected in a bridge circuit, these effects are reduced to an important extent. Because geometrically the two measuring cells are not completely identical, it may be necessary in connection with the accuracy and the reproducibility of the measuring system to accommodate the measuring block in a thermostated box, the sample gas, before entering the measuring cells, flowing through a heat exchanger which is thermally coupled with the box. The temperature of this box must be constant, for instance a few degrees of the maximum ambient temperature.

Figure 4:
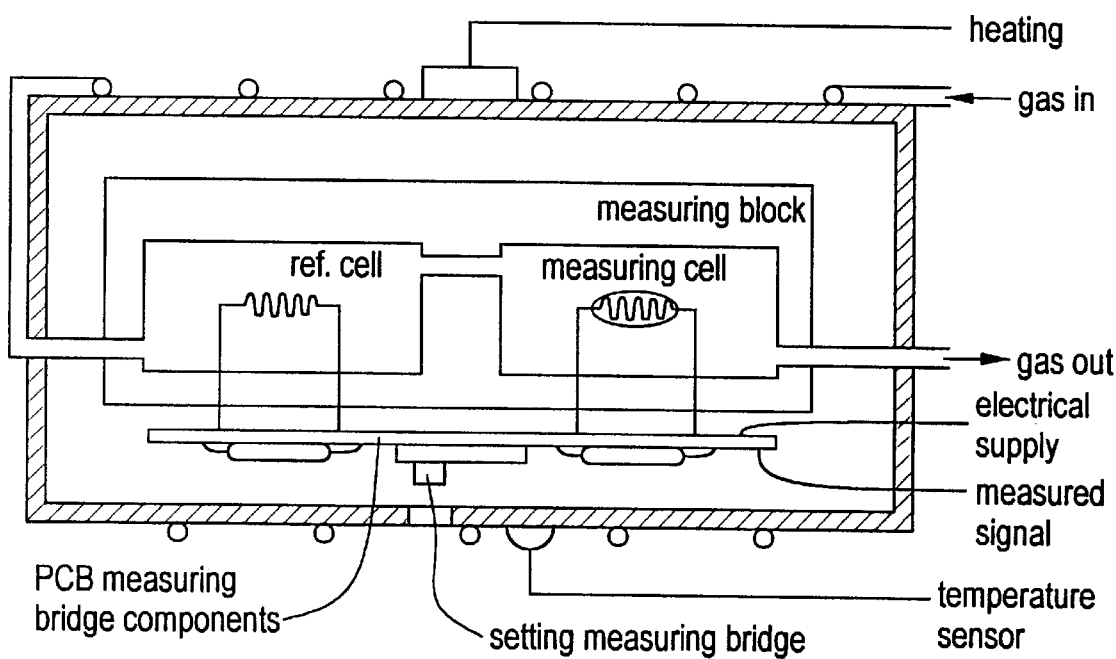
FIG. 4 is a schematic representation of one embodiment of a measuring block in accordance with the present invention.

A possible embodiment is shown in FIG. 4.

This figure shows a thermostated box in which, to improve the measuring accuracy and the stability, the measuring block including the two measuring cells and the components together constituting the electronic measuring bridge are accommodated. The wall temperature of the box is electronically controlled to a temperature approximately 10 degrees above the maximum ambient temperature. The electric current for the measuring bridge is supplied by an electronically stabilized supply.

Figure 5:
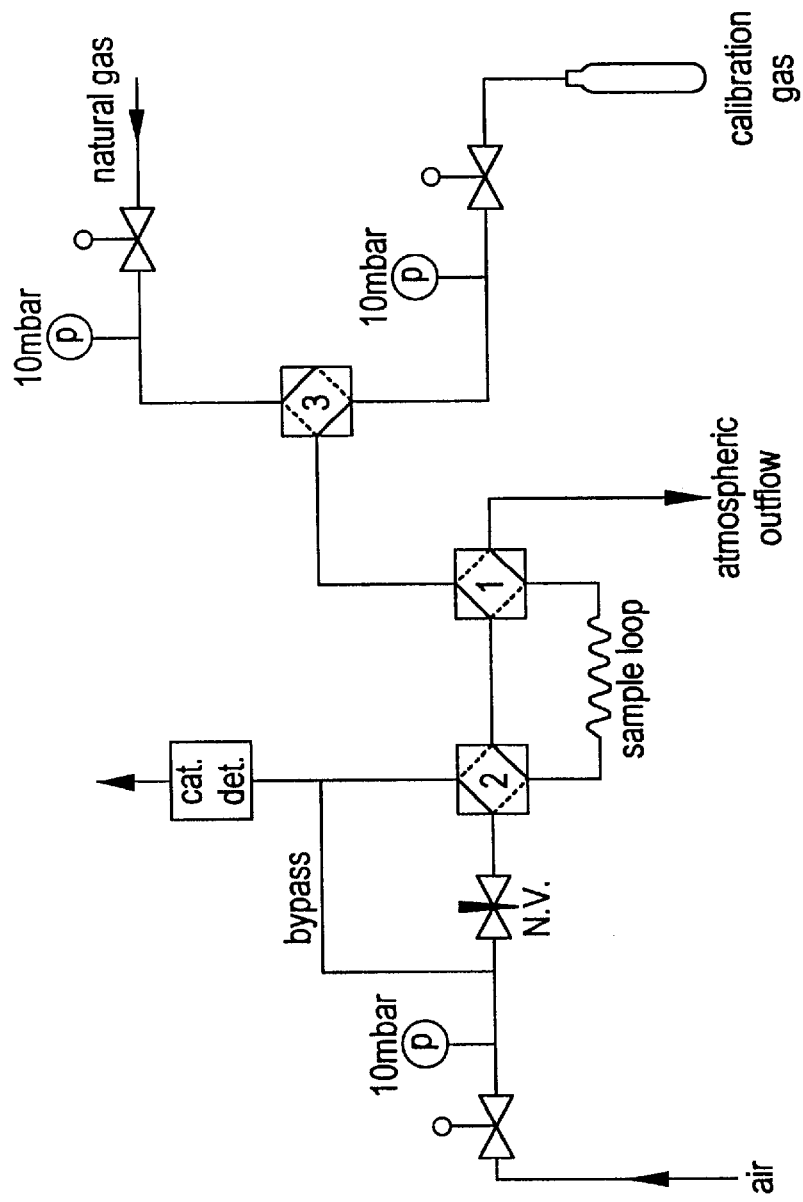
FIG. 5 is a schematic representation of one embodiment of a calorimeter in accordance with the present invention.

FIG. 5 shows a possible embodiment of the calorimeter according to the invention. The system is made up of three functional elements, viz. the sample selection, the sample taking and the bypass system.

For calibration a possibility of sample selection is built in. By adding switching valves, various calibration gasses can be connected to the measuring system.

The sampling system comprises two four-way cocks, nos. 1 and 2 and a sample loop. With this system it is possible to take an accurately reproducible amount of the gas to be examined. A first condition for this is an atmospheric outflow during flushing and a sample loop which is not unduly narrow, there being sufficient throughflow at a sample gas prepressure of approx. 10 mbar. A second condition is that the cocks 1 and 2 are consecutively switched with a short interval. By switching cock 1, the sample gas is isolated in the sample loop. By switching cock 2, this isolated amount of gas is passed via the bypass system into the supply conduit of the catalytic detector.

With this flow system, the influence of gas, prepressure and volume of the sample loop appear not to be critical for the measuring accuracy.

The bypass system controls the mixing of the gas to be measured with air. The concentration of gas, which should preferably not exceed the maximum limit of the detector, which is generally 5%, is controlled by the needle valve.

The required air can be supplied from a pressure cylinder. Because the prepressure is low, for instance approx. 10 mbar, it is also possible to provide the required air by including a pump in the discharge conduit of the catalytic detector, with ambient air being used. In that case, the supply conduit of the bypass system can optionally be provided with an active carbon filter to filter out any hydrocarbons and other combustible components present in the outside air.

In combination with this system, preferably a computer is used for processing the data into the calorific top value of the gas. With this computer, however, it is also possible to provide for the control of the entire sample taking.

In the case where the apparatus according to the invention is to be used for determining the Wobbe index of natural gas, in addition to the calorific top value ($H_s$), the density of the gas must be known as well.

$$WI = \frac{H_s}{\sqrt{d}}$$

If a suitable mass flow sensor is included in the supply conduit of the catalytic detector, the measuring system can also determine the Wobbe index. It is also possible to arrange this mass flow sensor in parallel with the calorimeter.

The signal of the mass flow sensor also has the shape of a Gaussian curve. The integral of this signal $S_m$ is a measure of the mass of the gas in the air sample.

$$d = C \int_{T_1}^{T_2} S_m dt - \text{background}$$

I claim:

1. A method for determining the calorific value of a combustible gas, comprising the steps of:
   providing an amount of combustible gas, said combustible gas comprising hydrocarbons;
   passing said amount of combustible gas through a hydrocarbon detection device comprising:
   a first measuring cell comprising a first filament disposed within a first combustion chamber which produces a first heating value;
   a second measuring cell comprising a second filament disposed within a second combustion chamber, said second measuring cell serially connected to said first measuring cell and including a catalyzing substance which produces a second heating value wherein said combustible gas first passed through said first and then through said second cell;
   said first measuring cell and said second measuring cell producing a signal indicative of a relationship between said first heating value and said second heating value; and
   integrating said signal to determine a value;
   comparing said value with standard calibrated values; and
   calculating the calorific value from said comparison.

2. The method according to claim 1, wherein said step of providing an amount of combustible gas further includes the step of providing a gas selected from the group consisting of natural gas, synthesis gas, fuel gas, refinery gas and pyrolysis gas.

3. The method according to claim 1, wherein said step of passing said amount of combustible gas through a hydrocarbon detection device, further includes the steps of flowing said gas through a sampling conduit, closing said sampling conduit, placing said sampling conduit in communication with a sampling stream, and passing the contents of said sampling conduit through said detection device.

4. The method according to claim 1, wherein said step of passing said amount of combustible gas through a hydrocarbon detection device, further includes the steps of flowing said gas through a sampling conduit, closing said sampling conduit, placing said sampling conduit in communication with a sampling stream, and passing the contents of said sampling conduit through said detection device.

5. The method according to claim 2, wherein said step of passing said amount of combustible gas through a hydrocarbon detection device, further includes the steps of flowing said gas through a sampling conduit, closing said sampling conduit, placing said sampling conduit in communication with a sampling stream, and passing the contents of said sampling conduit through said detection device.

6. A method for determining the Wobbe index of a combustible gas, comprising the steps of:
   providing an amount of combustible gas, said combustible gas comprising hydrocarbons;
   determining the density of said combustible gas;
   passing said amount of combustible gas through a hydrocarbon detection device comprising
   a first measuring cell comprising a first filament disposed within a first combustion chamber which produces a first heating value;
   a second measuring cell comprising a second filament disposed within a second combustible chamber, said second measuring cell serially connected to said first measuring cell and including a catalyzing substance which produces a second heating value wherein said combustible gas first passes through said first and then through said second cell; and
   said first measuring cell and said second measuring cell producing a signal indicative of a relationship between said first heating value and said second heating value;
   integrating said signal to determine a value;
   comparing said value with standard calibrated values;
   calculating a calorific value from said comparison; and
   determining said Wobbe index of said combustible gas from said calorific value and said density.

7. The method according to claim 6, wherein the step of determining the density of said combustible gas further includes the steps of:
   using a kathorometer to measure a heat conductivity value for said natural gas;
   comparing said measured heat conductivity value with a calibration value; and
   determining said density from said comparison.

8. The method according to claim 6, wherein said step of providing an amount of combustible gas further includes the step of providing a gas selected from the group consisting of natural gas, synthesis gas, fuel gas, refinery gas and pyrolysis gas.

9. The method according to claim 6, wherein said step of passing said amount of combustible gas through a hydrocarbon detection device, further includes the steps of flowing said combustible gas through a sampling conduit, closing said sampling conduit, placing said sampling conduit in communication with a sampling stream, and passing the contents of said sampling conduit through said detection device.

10. The method according to claim 7, wherein said step of passing said amount of combustible gas through a hydrocarbon detection device, further includes the steps of flowing said combustible gas through a sampling conduit, closing said sampling conduit, placing said sampling conduit in communication with a sampling stream, and passing the contents of said sampling conduit through said detection device.

11. Apparatus for determining the calorific value of a combustible gas comprising:

means for taking a sample of a gas;

means for generating a signal proportional to the calorific value of said gas comprising a first measuring cell comprising a first filament disposed within a first combustion chamber;

a second measuring cell comprising a second filament disposed within a second combustion chamber, said second measuring cell serially connected to said first measuring cell and including a catalyzing substance wherein said gas first passes through said first measuring cell which produces a first heating value and then through said second measuring cell which produces a second heating value;

and wherein said means for generating a signal produce a signal indicative of the relationship between said first heating value and said second heating value;

means for integrating said signal; and means for determining the calorific value by comparing the integrated signal with calibration values.

12. Apparatus for determining the Wobbe index of a gas comprising:

(a) means for taking a sample of a gas;

(b) means for determining the calorific value of said gas comprising means for generating a signal proportional to the calorific value of said gas comprising a first measuring cell comprising a first filament disposed within a first combustion chamber;

a second measuring cell comprising a second filament disposed within a second combustion chamber, said second measuring cell serially connected to said first measuring cell and including a catalyzing substance wherein said gas first passes through said first measuring cell which produces a first heating value and then through said second measuring cell which produces a second heating value;

and wherein said means for generating a signal produce a signal indicative of the relationship between said first heating value and said second heating value;

means for integrating said signal; and means for comparing the integrated signal with calibration values to determine the calorific value of said gas;

(c) means for determining the density of said gas; and (d) means for determining the Wobbe index of said gas from said calorific value and said density of said gas.

13. Apparatus according to claim 12 wherein said means for determining the density of said gas comprise a katharometer.

* * * * *

UNITED STATES PATENT AND TRADEMARK OFFICE
CERTIFICATE OF CORRECTION

PATENT NO : 5,807,749
DATED : September 15, 1998
INVENTOR(S) : Hörnemann

It is certified that error appears in the above-identified patent and that said Letters Patent is hereby corrected as shown below:

In column 3, line 67, $$"U_m=C_m\{(C_1+C_2)\Delta T_n-C_1T_g-C_rT_w\}"$$

should read $$"\Delta U_m=C_m\{(C_1+C_2)\Delta T_n-C_1T_g-C_rT_w\}".$$

Signed and Sealed this

Thirtieth Day of May, 2000

Attest:

Q. TODD DICKINSON

*Attesting Officer*    *Director of Patents and Trademarks*